United States Patent
Bouvier

(10) Patent No.: US 9,517,044 B2
(45) Date of Patent: Dec. 13, 2016

(54) SYSTEM AND METHOD TO AUTOMATICALLY ASSIST MOBILE IMAGE ACQUISITION

(75) Inventor: Bernard Bouvier, Eragny sur Oise (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 822 days.

(21) Appl. No.: 13/443,719

(22) Filed: Apr. 10, 2012

(65) Prior Publication Data

US 2012/0201359 A1 Aug. 9, 2012

Related U.S. Application Data

(63) Continuation of application No. 12/641,780, filed on Dec. 18, 2009, now Pat. No. 8,177,430.

(30) Foreign Application Priority Data

May 22, 2009 (FR) ...................................... 09 53407

(51) Int. Cl.
*G21K 1/02* (2006.01)
*A61B 6/00* (2006.01)

(52) U.S. Cl.
CPC ............. *A61B 6/547* (2013.01); *A61B 6/4405* (2013.01); *A61B 6/548* (2013.01)

(58) Field of Classification Search
CPC ........ A61B 6/4405; A61B 6/547; A61B 6/548
USPC ...... 378/102, 198; 701/1, 22–26, 36, 41, 49; 3/102, 198
See application file for complete search history.

(56) References Cited

U.S. PATENT DOCUMENTS

| | | | | |
|---|---|---|---|---|
| 4,894,855 A | * | 1/1990 | Kresse | 378/196 |
| 6,131,690 A | * | 10/2000 | Galando et al. | 180/411 |
| 6,702,306 B1 | | 3/2004 | Ockwell | |
| 6,814,490 B1 | | 11/2004 | Suhm et al. | |
| 6,834,220 B1 | * | 12/2004 | Bail | 701/25 |
| 2001/0044577 A1 | | 11/2001 | Braun et al. | |

(Continued)

FOREIGN PATENT DOCUMENTS

CA 2229347 A1 12/1999
CN 2655869 Y 11/2004

(Continued)

OTHER PUBLICATIONS

PCT Search Report and Written Opinion issued in connection with corresponding PCT Application No. PCT/US2010/055603 on Feb. 16, 2011.

(Continued)

*Primary Examiner* — Toan Ton
*Assistant Examiner* — Mona M Sanei
(74) *Attorney, Agent, or Firm* — Fletcher Yoder, P.C.

(57) ABSTRACT

A system and method to perform image acquisition of a subject is provided. The system includes a mobile device to move an imaging system across a floor, and a brake system that restrains movement of the mobile device. A controller includes a memory having program instructions to instruct a processor to perform the steps of: instructing movement of the mobile device in support of the imaging system to a first position for image acquisition of the subject; receiving feedback that the mobile device is located at the first position; and applying a brake force to restrain movement of the mobile device. The step of applying the brake force includes generating a vacuum in restraint of movement of the mobile device with respect to the floor.

15 Claims, 8 Drawing Sheets

(56) References Cited

U.S. PATENT DOCUMENTS

| | | | |
|---|---|---|---|
| 2003/0085368 A1* | 5/2003 | Kesil et al. | 250/559.36 |
| 2005/0173549 A1* | 8/2005 | Bash et al. | 236/51 |
| 2006/0114104 A1* | 6/2006 | Scaramozzino | 340/10.2 |
| 2006/0120512 A1* | 6/2006 | Watanabe | 378/198 |
| 2007/0179460 A1 | 8/2007 | Adahan | |
| 2007/0192910 A1 | 8/2007 | Vu et al. | |
| 2007/0299571 A1* | 12/2007 | Laberteaux et al. | 701/24 |
| 2008/0118036 A1 | 5/2008 | Jensen et al. | |
| 2008/0119714 A1 | 5/2008 | Meissner et al. | |

FOREIGN PATENT DOCUMENTS

| | | |
|---|---|---|
| CN | 2880613 Y | 3/2007 |
| DE | 4224614 A1 | 1/1994 |
| DE | 102005052784 B3 | 7/2007 |
| JP | 53-061891 A | 6/1978 |
| JP | 60-252004 A | 12/1985 |
| JP | 63186403 U | 11/1988 |
| JP | 11292278 | 10/1999 |
| JP | 2002-036055 A | 2/2002 |
| JP | 2005-331021 A | 12/2005 |
| JP | 2006-141669 A | 6/2006 |
| JP | 2008-246109 A | 10/2008 |
| JP | 2011229900 A | 11/2011 |
| WO | 9316633 A1 | 9/1993 |

OTHER PUBLICATIONS

French Search Report and Written Opinion dated Feb. 2, 2010, issued in connection with corresponding FR Application No. 0953407 filed Mar. 22, 2009.

Siemens AG; "Artis Zeego Multi-Axis System," www.medical.siemens.com, 2 pages (Dec. 15, 2009).

Unofficial translation of Chinese Official Action from Chinese Patent Application No. 201080064320.3 dated Apr. 23, 2014.

Unofficial translation of Chinese Search Report from Chinese Patent Application No. 201080064320.3 dated Mar. 26, 2014.

Unofficial translation of Japanese Official Action from JP Patent Application No. 2012-544516 dated Apr. 28, 2014.

Unofficial translation of Japanese Patent Office Notice of Allowance for corresponding JP Application No. 2012-544516 dated Feb. 5, 2015.

* cited by examiner

SYSTEM AND METHOD TO AUTOMATICALLY ASSIST MOBILE IMAGE ACQUISITION

CROSS-REFERENCE TO RELATED APPLICATIONS

This application is a continuation of, and claims priority to, U.S. patent application Ser. No. 12/641,780, entitled "System and Method to Automatically Assist Mobile Image Acquisition", filed Dec. 18, 2009, which in turn is a continuation-in-part (CIP) of, and claims priority to, French Application No. 0953407 entitled "X-ray machine" filed on May 22, 2009, both of which are hereby incorporated by reference in their entirety.

BACKGROUND

The subject matter herein relates generally to image acquisition, and more specifically, to a method and arrangement to assist image acquisition of a subject. Although the foregoing description refers to medical imaging, the system is also applicable to industrial imaging.

Medical imaging systems encompass a variety of imaging modalities, such as x-ray systems, computerized tomography (CT) systems, and the like. Medical imaging systems generate images of an object, such as a patient, for example, through exposure to an energy source, such as x-rays passing through a patient. The generated images may be used for many purposes. For instance, internal defects in an object may be detected. Additionally, changes in internal structure or alignment may be determined. Fluid flow within an object may also be represented. Furthermore, the image may show the presence or absence of objects in the patient. The information gained from medical diagnostic imaging has applications in many fields, including medicine and manufacturing.

A certain conventional medical imaging system includes a mobile C-arm system. The mobile C-arm system can be used for general surgery, vascular procedures, and cardiac procedures, for example. The conventional mobile C-arm system is equipped with a radiological source or transmitter in opposed relation to a radiological detector (e.g., an image intensifier), and both are moved in relation to the imaged subject. With the subject positioned between the radiological source and detector, the C-arm system is moved and rotated so as to pass radiation through the imaged subject from various directions. As the radiation passes through the subject, anatomical structures cause variable attenuation of the radiation passing through the imaged subject and received at the detector. The detector translates the attenuated radiation into an image employed in diagnostic evaluations. In typical medical procedures around such imaging systems, multiple physicians, nurses, and technicians are located in close proximity to the imaged subject.

BRIEF SUMMARY

There is a need for a mobile imaging system that can be readily and automatically located in arbitrary positions in a crowded work environment. The above-mentioned needs are addressed by the embodiments described herein in the following description.

According to one embodiment, a method of mobile image acquisition of a subject is provided. The method comprises the steps of providing a imaging system supported on a mobile device so as to steer movement of the imaging system across a floor; releasing restraint of movement of the mobile device; instructing movement of the mobile device in support of the imaging system to a first position for image acquisition of the subject; receiving feedback that the mobile device is located at the first position; and applying a brake force to restrain movement of the mobile device, wherein the step of applying the brake force includes creating a vacuum in restraint of movement of the mobile device relative to the floor.

According to another embodiment, a system to perform image acquisition of a subject is provided. The system comprises an imaging system operable to perform image acquisition of the subject; a mobile device operable to move the image system across a floor; a brake system that restrains movement of the mobile device with respect to the floor; a controller in communication with the imaging system, the mobile device, and the brake system, the controller including a memory having a plurality of program instructions to instruct a process to perform the steps of: instructing movement of the mobile device in support of the imaging system to a first position for image acquisition of the subject, receiving feedback that the mobile device is located at the first position, and applying a brake force to restrain movement of the mobile device, wherein the step of applying the brake force includes creating a vacuum in restraint of movement of the mobile device relative to the floor.

According to yet another embodiment, a computer program product to control image acquisition by an imaging system supported on a mobile device to move across a floor is provided. The computer program product includes a computer readable medium having stored thereon computer executable instructions for execution by a processor to perform the steps of: instructing movement of the mobile device in support of the imaging system to a first position for image acquisition of the subject; receiving feedback that the mobile device is located at the first position; and applying a brake force to restrain movement of the mobile device, wherein the step of applying the brake force includes creating a vacuum in restraint of movement of the mobile device relative to the floor.

Systems, methods, and computer program products of varying scope are described herein. In addition to the aspects and advantages described in this summary, further aspects and advantages will become apparent by reference to the drawings and with reference to the detailed description that follows.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
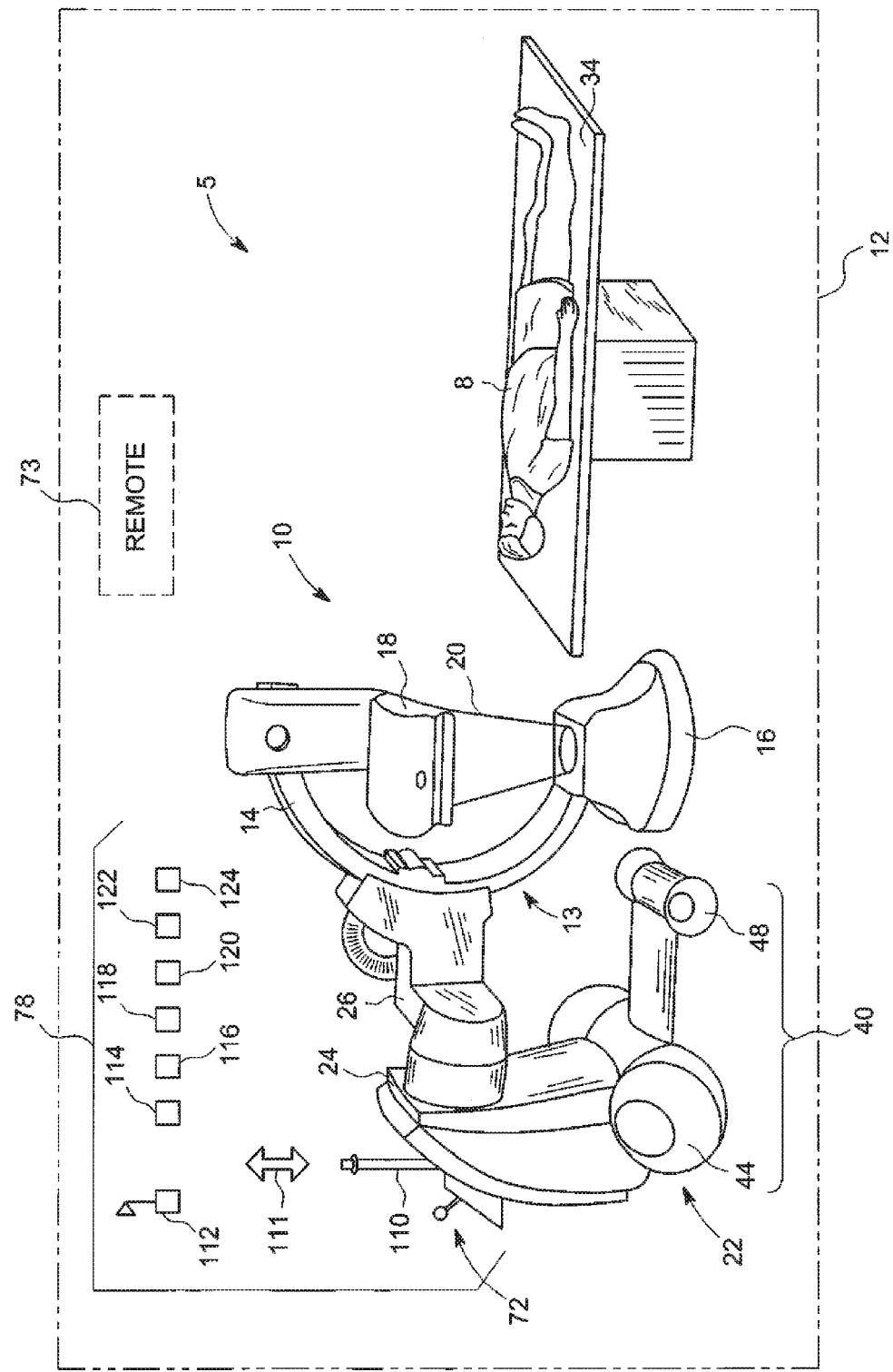
FIG. 1 shows a schematic diagram of an embodiment of a mobile imaging system of the subject matter described herein.

FIG. 1 shows a system 5 to image acquisition of a subject or patient 8 of the subject matter described herein. An embodiment of the system 5 can include an imaging system such as an X-ray machine 10 operable to pass X-rays through the subject or patient 8 and then detect and process acquired image data for interpretation. Yet, the type of imaging system (e.g., computerized tomography (CT), ultrasound (US), electron beam tomography (EBT), magnetic resonance (MR), fluoroscopic, angiographic, positron electron emission (PET), etc.) can vary.

One embodiment of the X-ray machine 10 is a vascular type and located in an examination room or operating room or hybrid room (represented in the form of a frame referenced 12). The X-ray machine 10 can be operated remotely, for example so that an operator can be shielded from the radiation. Alternatively, the X-ray machine 10 can be placed in the examining or operating room 12 so that a health care provider can view acquired image data while performing a medical procedure on the patient 8.

The X-ray machine 10 can include a gantry 13 comprising an arm 14 that can rotate in at least two dimensions of space around the patient 8. The arm 14 can be generally C-shaped and in support of an X-ray tube 16 which is the X-ray source at one of its ends and a detector 18 at another of its ends. Yet, the shape of the arm 14 can be curvilinear, angular, circular or O-shaped, etc. and is not limiting on the subject matter described herein. Examples of the arm 14 can be C-shaped as manufactured by GENERAL ELECTRIC® Corporation, the mobile C-shaped arm as manufactured by Ziehm Imaging Incorporated, and the O-ARM® as manufactured by MEDTRONIC® Inc. The x-ray tube 16 can be generally operable to send an X-ray beam 20 along a direction of emission.

The detector 18 is hooked to the arm 14 opposite the tube 16 and in the direction of emission. The X-ray tube 16 and the image detector 18 can be mounted at the opposite ends of the arm 14 so that the X-rays emitted by the tube 16 can be incidental to and detected by the detector 18. The detector 18 can be connected to a lift (not shown) used to raise and lower the detector 18 in the direction of emission.

For example, during a radiography exposure, the x-ray tube 16 and the detector 18 can be positioned so that when, for example, the patient 8 is interposed between the X-ray tube 16 and the detector 18, and is irradiated by X-rays, the detector 18 produces data representing characteristics of the interposed patient 8 that can be conventionally displayed on a monitor (not shown) and stored electronically.

An embodiment of the arm 14 can be mounted on a mobile carriage or mobile platform or mobile device 22 through a support element 24. The support element 24 can be mounted fixedly on the mobile device 22. The arm 14 can be connected to the support element 24 by a rotating arm 26. The arm 14 can be mounted so as to be sliding relative to the rotating arm 26. The rotating arm 26 can rotate about an axis passing through the X-ray beam 20. This rotating assembly of the rotating arm 26 on the support element 24 can enable the X-ray tube 16 and the image detector 18 to move rotationally along or around the arc-shape of the rotating arm 26. The arm 14, the support element 24, and the rotating arm 26 can be hinged relative to one another to enable the X-ray machine 10 to move the x-ray tube 16 and detector 18 in generally three dimensions to achieve images of the internal organ of the patient 8 to be examined at different values of incidence. By combining the motion of rotation of the moving parts of the X-ray machine 10, the X-ray beam 20 can describe all the directions of sending of the X-rays included within a sphere.

Figure 2:
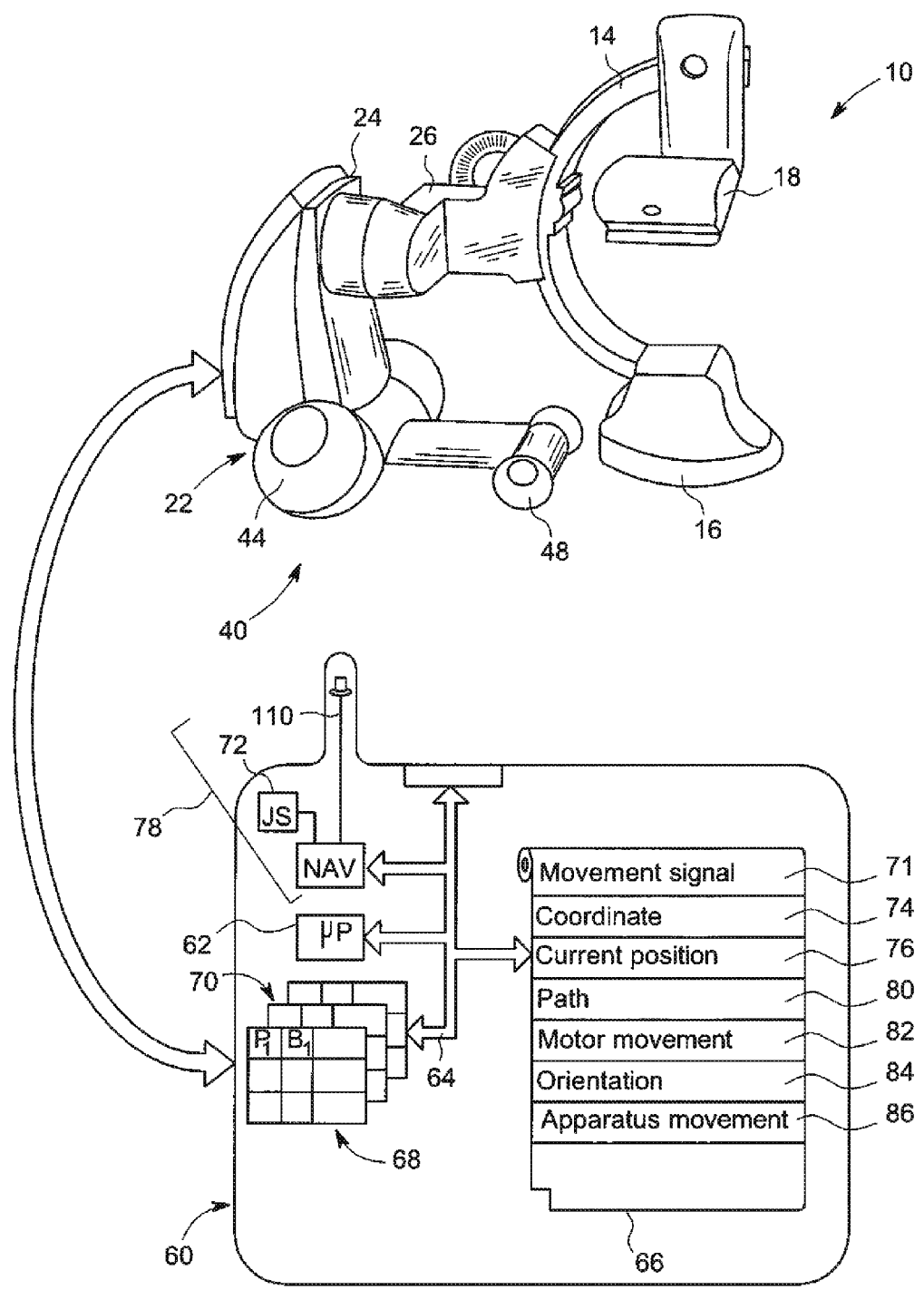
FIG. 2 shows a detailed schematic diagram of an embodiment of a brake system to selectively restrain movement of the mobile platform assembly and imaging system of FIG. 1, the brake system in a stand-by or retracted state.
Figure 3:
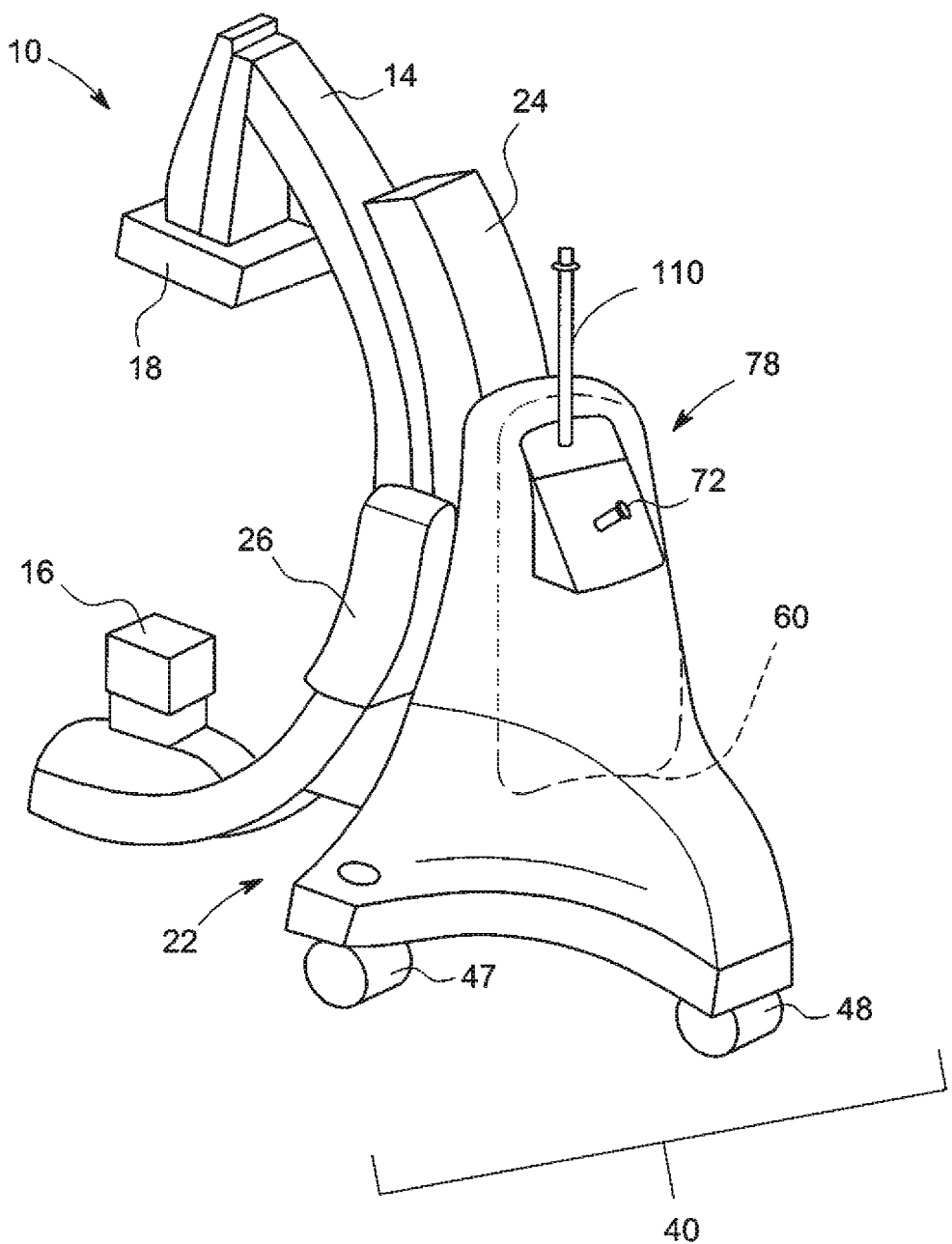
FIG. 3 shows a detailed schematic diagram of an embodiment of a brake system to selectively restrain movement of the mobile platform assembly and imaging system of FIG. 1, the brake system in restraint of movement or clamped state of the mobile device and imaging system of FIG. 1.

The embodiment of the mobile device 22 can be generally configured to move the X-ray machine 10 on the ground. An embodiment of the mobile device 22 can include a wheeled or roller system 40 operable to move or shift the mobile device 22 in every direction of the plane represented by the ground, including rotation of the mobile device 22 about a vertical axis passing through the X-ray beam 20. An embodiment of the roller system 40 comprises at least one motor driven and guide wheel 44 and at least one free wheel 48. Another example of the roller system 32 may include holonomic wheels. The type of wheeled or roller system 32 can vary. FIG. 2 illustrates an embodiment of the mobile device 22 that includes two motor-driven and guide wheels 44 placed in the rear of the mobile device 22 opposite the arm 14. FIG. 3 illustrates an embodiment of the mobile device 18 that includes two motor-driven and guide wheels 44 placed toward the front and one free wheel located toward the rear opposite the front. The number and location of the motor driven and guide wheels 44 or free wheel(s) 48 can vary.

The mobile device 22 can also include a drive (e.g., electric, pneumatic, hydraulic, etc.) 50 operable to move the wheels 44, 48. An embodiment of the drive 50 can include a direction motor coupled to a driving motor. The connection of the wheels 44, 48 to the drive 50 can be accordingly to that known to those skilled in the art. The mobile device 22 can be electrically powered in a fashion independent of that of the X-ray machine 10.

The x-ray machine 10 can be operated in combination with an examination table or bed 34 on which the patient 8 reclines. The X-ray machine 10 can be shifted, moved or positioned in a working mode so that the examination table 34 is placed within the C-shape of the arm 14 such that the x-ray tube 16 can be located beneath the examination table 34 and the detector 18 located above the examination table 34 or vice versa and the patient 8 to be examined positioned in the path of the X-ray beam 20.

As illustrated in FIG. 2, the X-ray machine 10 can include a control unit 60 to automatically control the drive 50 to move the wheels 44 of the mobile device 22. An embodiment of the control unit 60 can include a processor or microprocessor 62 connected to a bus 64, and a program memory 66 and data memories 68 and 70. The program memory 66 can be divided into several zones or modules, each module corresponding to a function or a mode of operation or action of the X-ray machine 10. An action can correspond to the implementation of one or more modules by the processor 62, connected to the program memory 66 in which the module is stored, of all or part of the instruction codes forming the module. Actions can be attributed to programs such that the actions can be executed by the processor 62, where the processor 62 can be controlled by instruction codes recorded in the program memory 66 of x-ray machine 10. These instruction codes can implement the means that the machine 10 can carry-out the action.

The discussion and illustration of the zones or memories 66, 68, 70 described herein are for example illustration of the layout of components and recordings of data. These zones or memories 66, 68, 70 can be unified or distributed according to constraints of size of the database and/or the speed of the processing operations desired.

One embodiment of the program memory 66 includes a zone 71 of instruction code to receive a movement signal corresponding to the activation of the position controls (e.g., buttons, touch-screen, toggle, joystick, etc.) 72 of the mobile device 22 or on the X-ray machine 10. The position controls 72 can also be part of a remote control unit 73.

A zone 74 can comprise instruction code to extract, from the data memory 68, the coordinates of the position to be attained by the X-ray machine 10, on the basis of the received signal described above with respect to zone 70.

The zone 74 of instruction code can be in communication with or command a navigation system 78 in order to determine the coordinates of the current position of the X-ray machine 10. The navigation system 78 can comprise manual position controls 72 to control movement of the mobile device 22 and/or the drive system of the arm 14 of the X-ray machine 10. One embodiment of the position controls 72 can control movement of the mobile device 22 in various directions (e.g., forward, backward, leftward or rightward) as well as control similar shifts to image acquisition (e.g., panoramic view, horizontal, vertical and zooming). The navigation system 78 can be operable to convert a shift or movement of the position controls 72 into electrical signals that can be interpreted by the control unit 60 of the mobile device 22. The joystick 79 can thus control movement of the mobile device 22 in a pre-programmed trajectory desired by the operator.

A zone 80 can comprise instruction code to command the navigation system 78 in order to establish a path of movement, from the current position and from the position to be attained of the x-ray machine 10.

A zone 82 can comprise instruction code to command operation, activation, working, or movement of the drive 50.

A zone 84 can comprise instruction code to receive a work orientation signal for the arm 14 of the X-ray machine 10 corresponding to the actuation of the orientation commands for image acquisition of the patient 8. These orientation and position commands can be distinct.

A zone 86 can comprise instruction code to command movement of the X-ray machine 10 moving parts, including the arm 14, the rotating arm 26, the support element 15 and/or the roller system 40. The movement of these parts 14, 24, 26, 40, as a function of the orientation signal, can be done such that the region of interest of the patient 8 to be imaged remains positioned within the X-ray beam 20.

An embodiment of the data memory 68, 70 can include predetermined parking and working positions. A parking position can be a place or location where the X-ray machine 10 can be positioned when in parking or idle mode outside a restricted space needed for a medical procedure. A working position can be a place or location where the X-ray machine 10 to perform image acquisition of the patient 8. One example of the data memory 68, 70 can be structured in a table format of rows and columns, where each row corresponds to the coordinates of a position of the X-ray machine 10 and each column corresponds to a piece of information on this position of the X-ray machine 10. For example, a row can correspond to the coordinates of a predetermined working position or parking position of the X-ray machine 10 and a column can correspond to a shift signal associated with the actuation of a given positional command of the X-ray machine 10.

The data memory 68, 70 can also include predetermined working orientations for the moving parts 14, 24, 26 of the X-ray machine 10 or the roller system 40. A working orientation can be a configuration of the X-ray machine 10 where the arm 14, the support element 24, the rotating arm 26, and the roller system 40 can shift or move into a radiography position according to the orientation signal. This shift may not affect the position of the region of interest of the patient 8 to be examined relative to the X-ray beam 20.

An embodiment of the data memory 68, 70 can be structured in a table format of rows and columns, where each row corresponds to a working orientation of the moving parts 14, 24, 26 or 40 of the X-ray machine 10 and each column corresponds to a piece of information on this orientation. For example, rows can correspond to the movements to be made by each moving part 14, 24, 26, or 40 and columns can correspond to movement signals associated with the actuation of a given orientation command of the X-ray machine 10. The positional and orientation command may be actuated simultaneously or consecutively.

Figure 4:
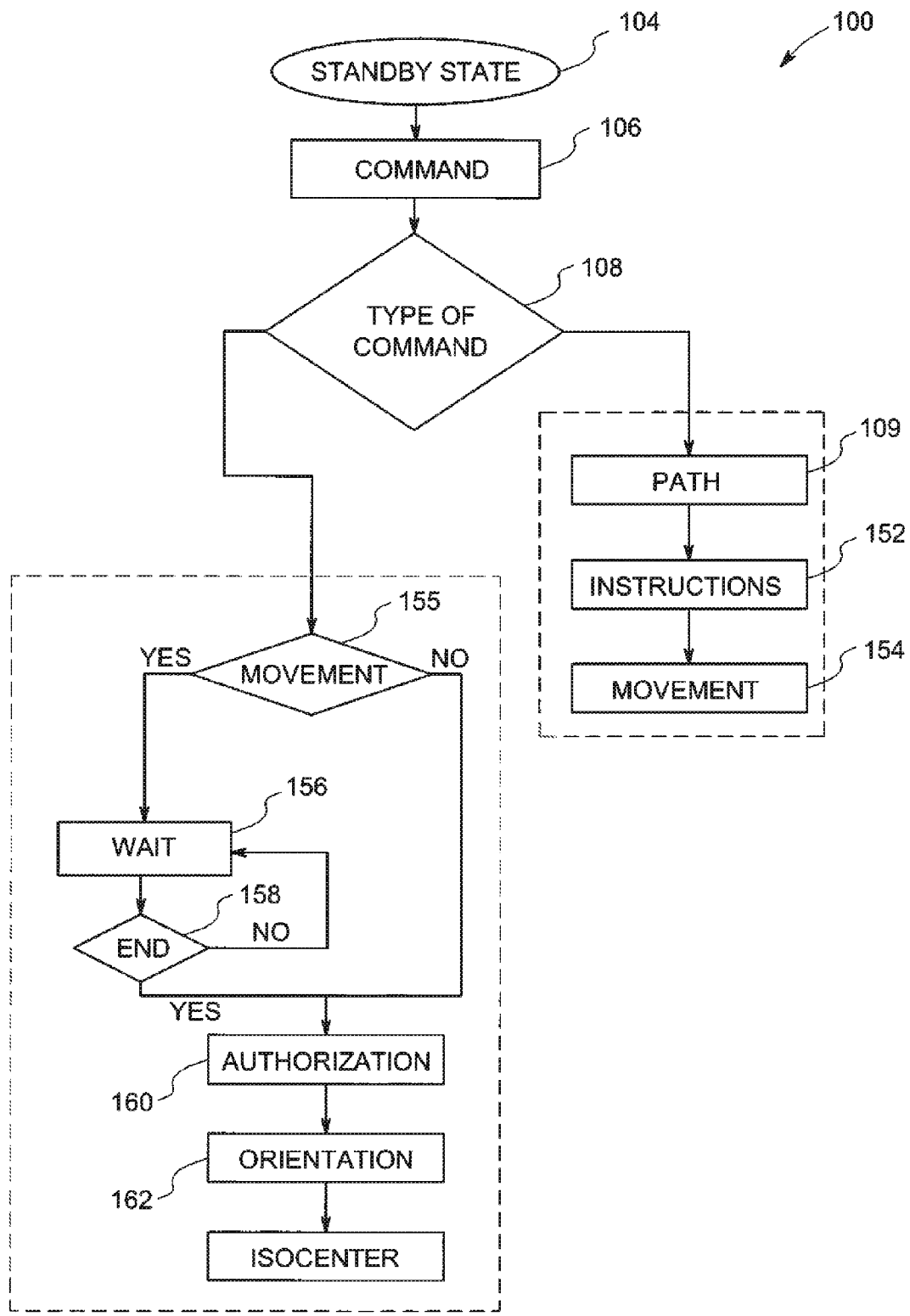
FIG. 4 shows a schematic flow diagram of an embodiment of a method of navigating the mobile device in combination with the imaging system of FIG. 1.

FIG. 4 shows an embodiment of a method 100 of the subject matter herein. A first preliminary step 104 can include putting the X-ray machine 10 in a standby mode. Step 106 can include receiving a positional or orientation command of the X-ray machine 10.

Step 108 can include identifying the type of acquired signal (e.g., positioning signal). Step 109 can include computing a path to place the X-ray machine 10 in the desired position per the received positional signal in step 106. To achieve this end, the control unit 60 can activate the navigation system to: compute the current position of the X-ray machine 10; compute an optimum or pre-programmed trajectory between the current position and the coordinates contained in the positional signal received in step 106; and guide movement of the X-ray machine 10 by reference to this path.

In one embodiment, the navigation system 78 can include a wireless communication or tracking system (e.g., including an antenna, transceiver, receiver, emitter or transmitter or combination thereof) 110 in wireless communication or link (e.g., global satellite positioning (GPS), radiofrequency, infrared, optical recognition of bar codes or shapes, ultrasound, electromagnetism, etc.) 111 with various stationary receivers or transmitters having either a unique identification code or positional coordinate. The stationary receivers or transmitters may be positioned at a height and/or on the ground and/or on the ceiling or on the table 34.

For example, the navigation system 78 can include wireless tags (e.g., electromagnetic, radio frequency, ultrasonic, infrared, optical, etc.) 112 provided with a battery that gives them the energy needed to transmit a low frequency, medium frequency or high frequency signal over a distance (e.g., from one centimeter to a few centimeters). Wireless tags 112 may be autonomous from an energy point of view to activate in response to a variable electromagnetic or radiofrequency signal.

The navigation system 78 can be generally operable to exchange or compute position coordinates of the X-ray machine 10 relative to predefined path or trajectory. On the basis of the position coordinates, the navigation system 78 can compute a current position and compute a trajectory or path or correction thereof relative to the predefined trajectory.

One example of the navigation system 78 can include optical readers operable to read or decode barcodes (e.g., two-dimensional) 114 representative of two-dimensional coordinates of their position in the environment (e.g., on the ground of the room 12 and/or on the ceiling or on the table 34) of the X-ray machine 10. The navigation system 78 can include an optical reader designed to decode the information contained in the barcodes. The optical reader can be placed beneath the mobile device 22 facing the ground and/or above the mobile device 22 facing the ceiling or in any variant facing direction therebetween so as to detect and read the bar code. From the coordinates of the position of the barcode 114, the navigation system 78 can compute the current position and compute a trajectory and corrects the trajectory of the X-ray machine 10 or mobile device 22 relative to a preliminarily computed or pre-programmed trajectory.

In another embodiment, the navigation system 78 can be in communication with a GPS or global positioning system 116 so as to be operable to compute the current position of the X-ray machine 10, its trajectory or path, or its the pre-programmed trajectory.

Another example of the navigation system 78 can include a system 118 of optical or laser emitter and/or detectors operable to perform general real-time tracking of position and updated path or trajectory or correction thereof to locate X-ray machine 10 supported on the mobile device 22. The system 118 of laser emitters and/or detectors can be located at one or stationary locations in communication with the navigation system 78 of the X-ray machine 10 or mobile device 22. In response to receiving a positioning signal according to a predefined trajectory or manual input, the navigation system 78 can activate emission of a laser beam and measurement the duration between the incident laser beam and the reflected laser beam. Based on the measured duration, the navigation system 78 can compute the current position of the X-ray machine 10 or mobile device 22 relative to an optimal or pre-programmed trajectory, and can generate signals to steer the mobile device 22 relative to the optimal or preprogrammed trajectory or path, and adjustments thereto accordingly. An embodiment of the system 118, the wireless tracking system 110 can be a laser emitter mounted on the mobile device 22 or system 5. The laser emitter 110 can rotate and measure the distance between the system 5 and one or more the reflectors stationed at the walls of the room.

In another embodiment, the navigation system 78 can include an electromagnetic field link 120 to define the path or trajectory of the X-ray machine 10 or mobile device 22. The navigation system 78 can detect the position of the X-ray machine 10 and/or mobile device 22 dependent on the electromagnetic filed link 120 to steer the path or trajectory of the X-ray machine 10 and/or mobile device 22 relative to a pre-computed or pre-programmed trajectory or path.

In another embodiment, the navigation system 78 can include an optical guidance system 122 having longitudinal markings that constitute a reference for the trajectory of the X-ray machine 10 and/or mobile device 22. The optical guidance system 122 can include a camera or similar device at the forward part of the mobile device 22 to form an image of the path of the mobile device 22 or X-ray machine 10. Depending on the data communicated from the optical guidance system 122 to the control unit 60, the control unit 60 can compute the position of the X-ray machine 10 and/or mobile device 22 and correct the trajectory or path relative to a pre-computed or pre-programmed trajectory.

Another embodiment of the optical guidance system 122 can include at least one camera in communication with the X-ray machine 10 and/or mobile device 22 from a stationary position in the room 12. The control unit 60 can be operable to process acquired data from the optical guidance system 122 and compute an environment or landscape with a predetermined vicinity or threshold of the X-ray machine 10 and/or mobile device 22, including detection of potential obstacles. The control unit 60 can compute the position or location of the X-ray machine 10 and/or mobile device 22 and correct its trajectory relative to a pre-computed or pre-programmed trajectory.

In another embodiment, the navigation system 78 can include sensors (e.g., accelerometers) 124 capable of measuring a direction and/or magnitude of shift or movement) of the X-ray machine 10 and/or roller system 40 of the mobile device 22. Based on these acquired measurements, the control unit 60 can use odometry techniques to compute the position of the X-ray machine 10 and/or mobile device 22. Starting from a known initial position and computing the measured movements, the control unit 60 can compute the current position of the X-ray machine 10 and/or mobile device 22. Depending on the result of this computation, the control unit 60 can correct the trajectory or path of the X-ray machine 10 and/or mobile device 22 relative to a trajectory a pre-computed or pre-programmed trajectory.

In another embodiment, the data memory 68, 70 can include information on a mapping of the environment of the X-ray machine 10, the mapping including reference coordinates of a predefined parking position of the X-ray machine 10.

Figure 5:
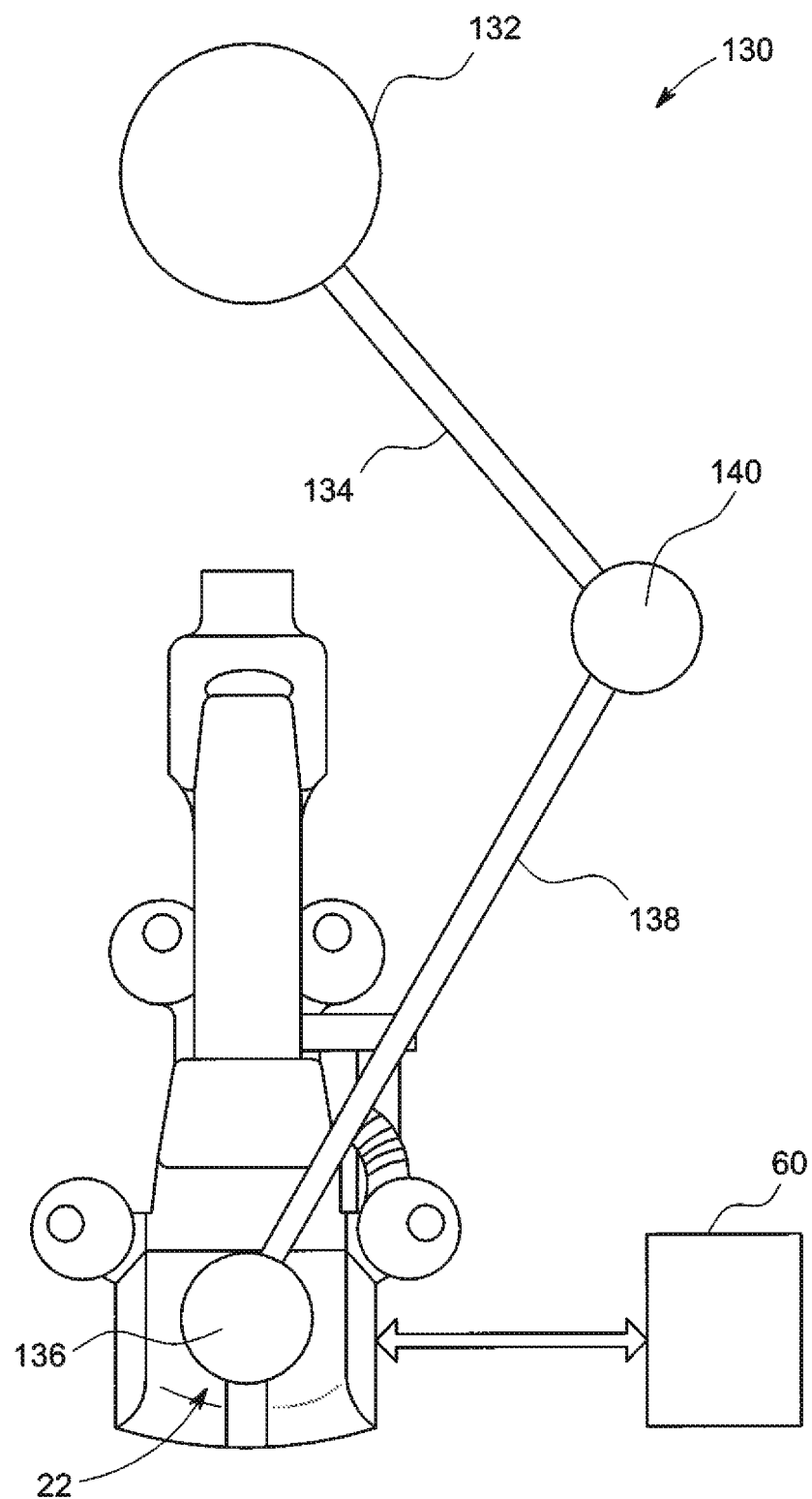
FIG. 5 shows a flow diagram of an embodiment of the mobile carriage system of FIG. 1 in management of transport and restraint of the imaging system of FIG. 1.

FIG. 5 describes another embodiment of the mobile device 22 of the X-ray machine 10 connected by a mechanical linkage 130 to a stationary platform (e.g., the ceiling or to the walls of the room 12) 132. One example of the mechanical linkage 130 can include a first arm 134 connected by a first hinge device 136 to the mobile device 22. This first arm 134 can be connected to a second arm 138 by a second hinge device 140. The number of arms and hinges can vary. This second arm 138 can be coupled 10 the hinge device 132 at the mobile device 22. The mechanical linkage 130 of hinged arms 134, 138 can include encoders (not shown) operable to convert detected mechanical movement of the arms 134, 138 into a numerical variable and communicate to the control unit 60, and the control unit 60 can combine the tracked angular position of the different encoders to guide or steer movement of the mobile device 22.

One or more of the above embodiments of the navigation system 78 or components thereof may be combined with others to refine the computation precision. The type of navigation system 78 can vary.

Step 150 can include communicating movement instructions to the drive of the mobile device 22. Step 152 can include controlling steering or guiding movement of the drive of the mobile device 22 through the pre-determined trajectory. The control unit 60 can steer or guide movement of the X-ray machine 10 via the mobile device 22 from a starting point to a position controlled by determining the position, the trajectory or pre-programmed trajectory, corrected if necessary, and cause corrections or changes in guidance with reference to this trajectory.

If the control unit 60 detects in step 108 that the type of received command signal is a navigation or an orientation signal, the control unit 60 can execute the following. Before processing the received orientation signal, step 155 can include computing if one or more of the above steps are being executed. If this is the case, step 156 can include storing or causing the navigation or orientation signal to sit idle without further processing. Step 158 can include computing a check as to whether the execution of one or more of the above steps is terminated in order to authorize the processing of the navigation or orientation signal. If no detection of execution of one or more of the above steps, step 160 includes authorizing further processing of this navigation or orientation signal.

Step 162 can include causing movement of the navigation or orientation of one or more of the arm 14, the support element 24, the rotating arm 26 and/or the roller system 40 to correspond to instruction in the navigation or orientation signal so as to position the X-ray beam 20 in a desired direction to perform image acquisition of the desired region of interest of the patient 8.

In the event of receiving a new orientation command, the control unit 60 can steer movement of the arm 14, the support element 24, the rotating arm 26, and/or the roller system 40 in a controlled manner and at a desired navigation or orientation while at the same time keeping X-ray beam 20 in the region of interest to be examined.

A technical effect of the subject matter described herein is to enhance changes in image acquisition with changes to the region of interest to be examined by moving the X-ray machine 10 via the roller system 40 of the mobile device 22 from one working position to another.

Figure 6:
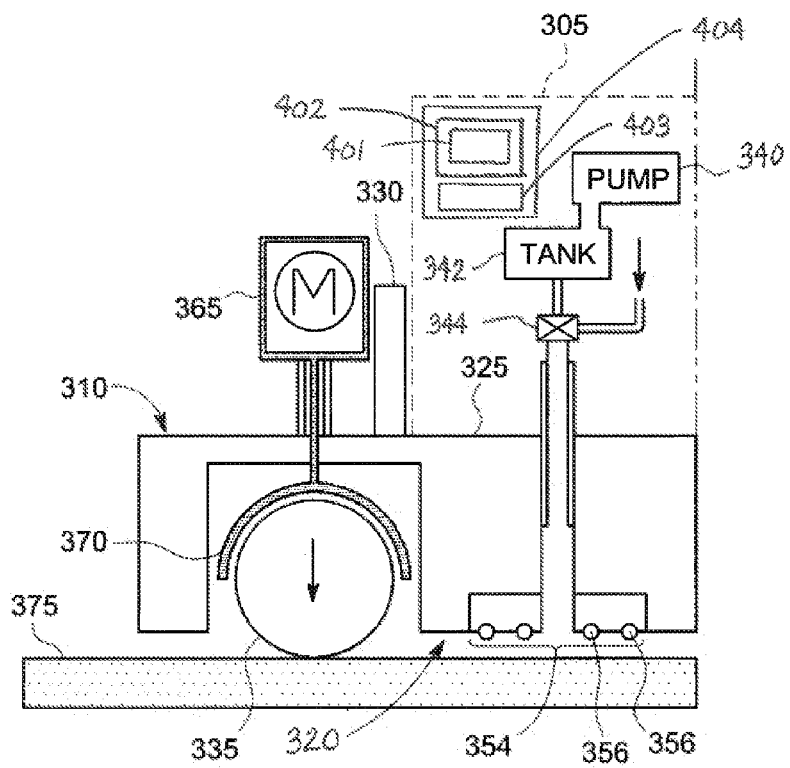
FIG. 6 illustrates an embodiment of an imaging system supported on a mobile device in combination with a braking system in accordance with the subject matter described herein, the braking system in a release state.
Figure 7:
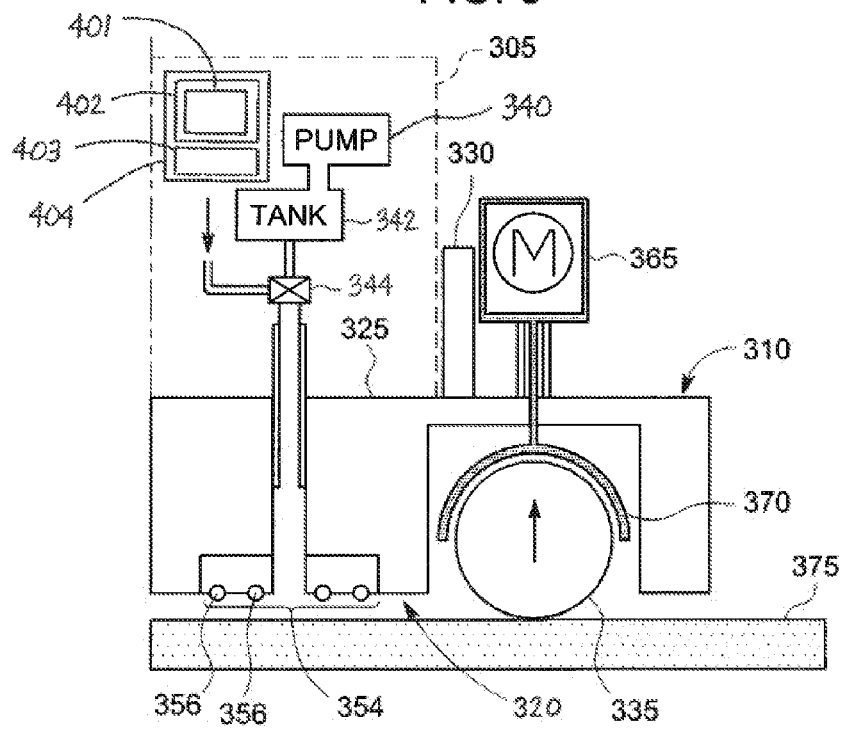
FIG. 7 illustrates an embodiment of an imaging system supported on a mobile device in combination with a braking system in accordance with the subject matter described herein, the braking system in a restraint state.

FIGS. 6 and 7 illustrate schematic diagrams of an imaging system 305 supported by an embodiment of the mobile carriage or platform or device 310, similar to the imaging system 5 supported on the mobile device 22 described above, in combination with a brake system 320 of the subject matter described herein.

The mobile device 310 generally includes a chassis or frame 325 in support of a motorized drive 330 to move one or more wheels 335 in mobile support of the chassis 325. The chassis 325 generally comprises a structural framework to support the imaging system 305 on the series of wheels 335. The motorized drive (e.g., electric motor, pneumatic motor, hydraulic motor, etc.) 330 can be generally configured to move the wheels 335 in support of the imaging system 305 on the chassis 325.

The embodiment of the brake system 320 can include vacuum operated portion having a vacuum pump 340, tank 342 and valve 344 in communication with a vacuum clamp (e.g., suction cup) 354 attached at the mobile device 310. The tank 342 can be in communication to provide a buffer reservoir of vacuum to more quickly create the vacuum force at the clamp 354. An embodiment of the vacuum clamp 354 can include a seal portion 356. With the seal portion 356 of the vacuum clamp 354 engaged against the floor, operation of the vacuum pump 340 can create a vacuum between the vacuum clamp 354 and the floor in restraint of movement of the mobile device 310 and imaging system 305 supported thereon.

The valve 344 can be generally located in communication between the tank 342 and the vacuum clamp 354. In a first position, the valve 344 can be operable to communicate the vacuum from the tank 342 to the vacuum clamp 354. In a second position, the valve can be generally operable to communicate the vacuum clamp 354 to atmosphere so as release the vacuum force at the clamp 354.

The embodiment of the brake system 320 can further include a motorized drive (e.g., electric, pneumatic, hydraulic, etc.) 365 operable to raise and lower the chassis 325 with respect to the wheel 335. The brake system 320 can include brake pads 370 operable to engage or contact the wheels 335 to restrain movement thereof when the motorized drive 365 lowers the chassis 325 with respect to the wheels 335. Lowering the chassis 325 such that the brake pads 370 engage in contact against the wheels 335 can also be configured to cause the vacuum clamp 354 to engage or contact the floor 375 or attachment thereto. With lowering of the chassis 325 such that the vacuum clamp 354 can be in contact with the floor, the force of the vacuum at the vacuum clamp 354 against the floor in combination with the force of restraint of the brake pad against the wheels 335 can work independently or in combination to restrain movement of the chassis 325 of the mobile device 310 and imaging system 305 supported thereon.

Figure 8:
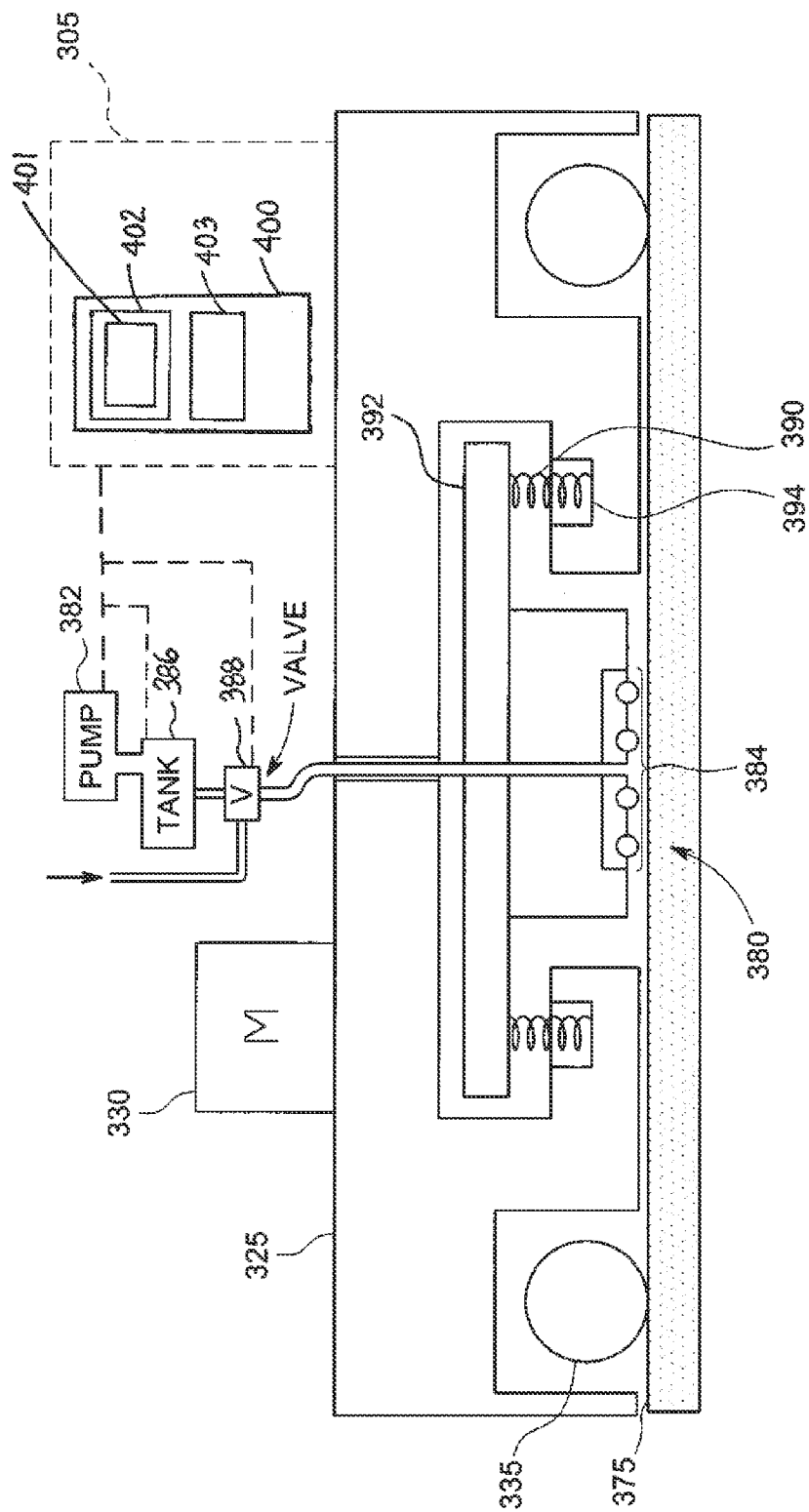
FIG. 8 illustrates another embodiment of an imaging system supported on a mobile device in combination with a braking system in accordance with the subject matter described herein, the braking system in a release state.

FIG. 8 illustrates another embodiment of the imaging system 305 supported by the mobile carriage or platform or device 310 in combination with a braking system 380 in accordance with the subject matter described herein, the braking system 380 in a release state. The braking system 380 can generally include the vacuum pump 382 in communication with a vacuum clamp 384, a tank 386 and a valve 388 therebetween, similar in function and operation as the vacuum pump 340, tank 342, valve 344, and vacuum clamp 354 as described above in FIGS. 6 and 7. The braking system 380 can further include a spring 390 bias of the vacuum clamp 384 to a raised position spaced at least a threshold distance to avoid interference of maneuvering of the mobile device 310.

Electrical power to or operation of the vacuum pump 382 can generate the vacuum at the tank 386. In response to an electrical signal, movement of the valve 384 to a first position can communicate the vacuum at the tank 386 so to cause the vacuum clamp 384 to engage or contact the floor and create the vacuum between the clamp 384 and the floor in restraint of movement of the mobile device 310 with respect to the floor 375. Upon interruption of electrical power to or operation of the vacuum to otherwise release of the vacuum at the vacuum clamp 384, the spring (e.g., compression spring or tension spring) 390 can bias the vacuum clamp 384 away from the floor to create the threshold spacing between the braking system 380 and the floor 375 to avoid interference with movement of the mobile device 310. According to another embodiment, an electrical signal to the valve 388 can cause the release of the vacuum at the clamp 384 to the atmosphere.

According to one embodiment, the spring 390 can be interconnected by a structural support 392 to the vacuum clamp 384. The spring 390 can be located between the structural support 392 and the chassis 325. Movement of the structural support 392 can be limited to a predefined displacement by contact with the chassis 325. The chassis 325 can include slots 394 to receive the spring 390 in bias against downward movement of the structural support 392. The spring 390 can be in tension and located above the structural support 392, or can be in compression and located below the structural support 392, so as to bias against downward movement of the vacuum clamp 384 toward the floor 375.

Having generally provided the above-description of a construction of the embodiment the system 300 having the mobile device 310 in combination with the brake system 320, 380 of the subject matter described herein, the following is a general description of a method 400 (See FIG. 10) of operation of the brake system 320, 380 in selective restraint of movement of the mobile device 310 in support of the imaging system 305. It should also be understood that the sequence or succession of the acts or steps of the method 400 as described in the foregoing description can vary. Also, it should be understood that the method 400 may not require each act or step in the foregoing description, or may include additional acts or steps not disclosed herein. One or more of following steps and acts of the method 400 can also be in the form of a computer program product 401 having modules or zones or computer-readable program instructions that can be stored on a computer readable medium or memory 402 for execution by a processor 403 of a controller or control unit or other computer programmable device 404, and which can be located or be integral at least in part with the program memory 66 in communication with the processor 64 of the control unit 60 described above or the imaging system 305 or remote unit 73 or be independent thereof.

Assume for sake of example that the mobile device 310 and the imaging system 305 supported thereon are located in a parked or stored position, and that the mobile device 310 is robotically operated and remotely or wireless controlled from a remote unit 396. The chassis 325 can be in a lowered position so that the brake pads 370 are engaged to restrain movement of the wheels 335. Although not required, the vacuum can also be maintained by the vacuum pump 382 at the vacuum clamp 384 in restraint of movement of the mobile device 310 at the stowed or parked position. Also assume that instructions to perform one or more of the following steps can be received via wireless communication from the remote unit 385 to the mobile device 310.

Figure 9:
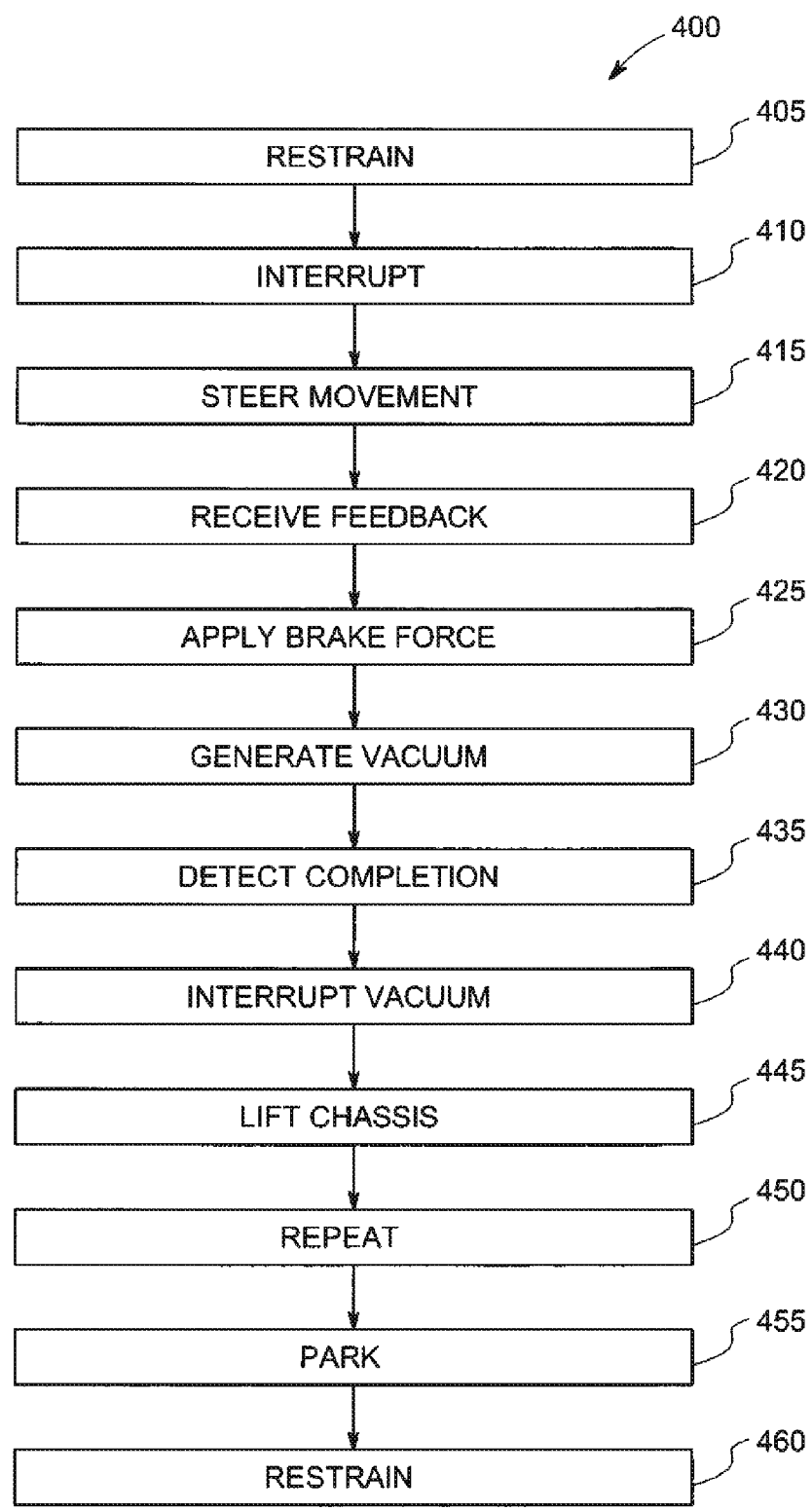
FIG. 9 illustrates a schematic flow diagram of an embodiment of a method of operating the brake system in combination with the mobile imaging system in accordance with the subject matter described herein.

Referring to FIG. 9, step 410 can include releasing restraint of movement of the mobile device 310. This step 410 can include interrupting electric power to or operation of the vacuum pump 382 so as to release the vacuum between the vacuum clamp 384 and the floor. Release of the vacuum can cause the spring 390 to bias and raise the vacuum clamp 384 from the floor. Step 410 can further include energizing the motorized drive 365 to raise or lift the chassis 325 and imaging system 305 supported thereon with respect to the wheels 335 so as to free movement of the wheels 335.

Step 415 can include instructing the motorized drive 330 to steer movement of the mobile device 310 in support of the imaging system 305 to a desired position with respect to the plate or insert 372 adjacent the table 34 for image acquisition of the subject 8. An embodiment of step 415 can include communicating instructions for the motorized drive 365 to steer the mobile device 310 and supported imaging system 305 to predefined locations and alignments with respect to the plate or inserts 372 according to a pre-defined type and/or body area and/or protocol of image acquisition to perform on the subject 8. Also, the mobile device 310 can receive manual instructions (e.g., via joystick) to selectively supplement movement of the mobile device 310 to the desired location.

Step 420 can include receiving feedback that the mobile device 310 and imaging system 305 are located at the desired alignment and location with respect to the patient support table 34 to perform image acquisition.

Step 425 can include applying the braking force to the mobile device 310. One embodiment of step 425 can include instructing the motorized drive 365 to lower the chassis 325 with respect to the wheels 335 so as to engage the brake pads 370 in contact with respect to the wheels 335 in restraint of movement of the mobile device 310. Step 425 can further include lowering the vacuum clamp 384 in contact or engagement with the floor 375.

Step 430 can include communicating electrical power to energize the vacuum pump 382 to generate a vacuum at the vacuum clamp 384 so as to cause the vacuum clamp 384 to engage against the floor against the bias of the spring 390. Step 430 can further include communicating an electrical signal to the valve so as to communicate the vacuum at the tank 386 to the clamp 384, so as to create a faster response to create a brake force. The restraint of the vacuum at the vacuum clamp 384 relative to the floor in combination with the location and brake force applied by the brake pads 370 at the wheels 335 of the chassis 325 can restrain vibration or tilting of the imaging system 305 in performing image acquisition (e.g., including during high-speed acceleration and deceleration in positioning the C-arm 14 (See FIG. 1) or for three-dimensional image acquisition).

Step 435 can include detecting completion of image acquisition at the present location of the mobile device 310 and imaging system 305.

Step 440 can include interrupting electric power to or operation of the vacuum pump or release of the vacuum generated at the vacuum clamp 384 so as to release restraint of movement of the vacuum clamp 384 relative to the floor. Step 440 can include communicating a signal to the valve 388 so as move to the second position and release the vacuum at the vacuum clamp 384 to the atmosphere.

Step 445 can include lifting the chassis with respect to the wheels 335 so as to remove restraint of the mobile device 310.

Step 450 can include repeating the above-described steps 410 through 445 in performing addition image acquisition at other selected locations around the periphery of the patient support table 34.

Step 455 can include receiving instructions to move the mobile device 310 and imaging system 305 supported thereon to the parked or stowed position.

Step 460 can include restraining movement of the mobile device 310, including lowering the chassis 325 so as to engage or contact the brake pads 370 in restraint of movement of the wheels 335 at the stowed position.

One or move of the above-described steps of the method 400 can be according to a pre-programmed protocol selected from a plurality of image acquisition protocols or therapeutic protocols dependent on an input or desired diagnosis received at the system 5. The preprogrammed protocol can include automatically causing application of the brake force by the brake system 320, 380 of the mobile device 310 in response to detecting proper alignment/position of the system 305 so as to ready for image acquisition. Likewise, the preprogrammed protocol can include causing automatic release of the brake force by the brake system 320, 380 in response to detecting complete of image acquisition at the current alignment/position.

Although the above description of the systems 5, 300 and method 400 are described with respect to image acquisition of the subject 8 supported on table 34, it should be understood that the mobile device 310 and imaging system 10, 305 supported thereon can be employed in a variety of applications (e.g., airport screening, industrial or commercial applications, etc.) and is not limiting on the subject matter described herein.

Although the above description of the systems 5, 300 and method 400 are described with respect to image acquisition of the subject 8 supported on table 34, it should be understood that the mobile device 310 and imaging system 305 supported thereon can be employed in a variety of applications (e.g., airport screening, industrial or commercial applications, etc.) and is not limiting on the subject matter described herein.

A technical effect of the above-described system 5 and 300 and method 400 includes providing force to restrain movement of the imaging system 10, 305 during image acquisition. The brake system 320, 380 increases the stability reduces risk of tilting or vibration of the imaging system 10, 305 during image acquisition that if otherwise uncontrolled may affect image quality and increase risk to safety of personnel or the imaged subject 8.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An X-ray machine comprising:
    an X-ray tube configured to emit an X-ray beam along a direction of emission,
    an X-ray detector situated opposite the tube and in the direction of emission of the X-ray beam,
    a mobile device on which the X-ray tube and X-ray detector are mounted, wherein the mobile device comprises a control unit comprising a processor, one or more memories, and a navigation system to drive the X-ray machine in a room, wherein the processor utilizes a map of the room and a working position stored in the one or more memories and a current position determined by the navigation system to establish a path of movement from the current position to the working position and to move the X-ray machine along the path of movement, and wherein the one or more memories store a table for use by the processor, wherein one of directional elements of the table store position coordinates within the room and a perpendicular set of directional elements of the table store instructions regarding the position of the X-ray machine.

2. The X-ray machine according to claim 1, wherein the mobile device comprises a roller system configured so as to make the X-ray tube rotate about a vertical axis passing through the X-ray beam.

3. The X-ray machine according to claim 2, wherein the roller system has at least one guide and motor wheel and at least one free wheel or holonomic wheels.

4. The X-ray machine according to claim 2, wherein the navigation system comprises sensors for measuring the movement of the roller system.

5. The X-ray machine according to claim 1, wherein the navigation system comprises a communications module using radioelectrical links installed in the mobile device and radiofrequency position identifier devices pre-installed in the room.

6. The X-ray machine according to claim 1, wherein the navigation system comprises a GPS localizing system.

7. The X-ray machine according to claim 1, wherein the navigation system comprises a laser beam emitter borne by the mobile device and laser signal detectors pre-installed in the room.

8. The X-ray machine according to claim 1, wherein the navigation system comprises an optical barcode reader installed in the mobile device and barcodes comprising positioning data pre-installed in the room.

9. The X-ray machine according to claim 1, wherein the navigation system comprises an electrical wire placed in the room configured to create an electromagnetic field detected by sensors placed on the mobile device.

10. The X-ray machine according to claim 1, wherein the navigation system comprises an optical guidance system configured to detect a longitudinal marking made in the room and constituting a reference for the trajectory of the mobile device.

11. The X-ray machine according to claim 1, wherein the navigation system comprises a joystick configured to control the movement of the mobile device.

12. The X-ray machine according to claim 1, wherein the mobile device is fixed to a wall of the room via one or more hinged arms.

13. The X-ray machine according to claim 1, wherein the instructions regarding the position of the X-ray machine comprise one or more shift signals associated with the actuation of a given positional command for the X-ray machine.

14. A method for the automatic moving of an X-ray machine, comprising:
    using a processor found within a control unit of the X-ray machine, computing a trajectory from a current position of the X-ray machine determined by a navigation system of the control unit to a working position stored in a memory accessible to the processor, wherein the memory further stores position coordinates within a room being navigated and instructions regarding the movement of the X-ray machine at each coordinate; and
    based on one or more commands issued by the processor, moving a mobile device on which the X-ray machine is mounted across the computed trajectory.

15. The method of claim 14, further comprising: determining the current position prior to computing the trajectory.

* * * * *